(12) United States Patent
Pitochelli

(10) Patent No.: US 6,602,442 B1
(45) Date of Patent: *Aug. 5, 2003

(54) COMPOSITION FOR GENERATING CHLORINE DIOXIDE

(75) Inventor: Anthony R. Pitochelli, Witchita, KS (US)

(73) Assignee: Vulcan Chemicals, Birmingham, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/689,236

(22) Filed: Oct. 12, 2000

Related U.S. Application Data

(63) Continuation-in-part of application No. 09/257,627, filed on Feb. 25, 1999, now Pat. No. 6,197,215.

(51) Int. Cl.$^7$ .................. A01N 59/08; A61K 33/14; A62D 3/00; C01B 7/00

(52) U.S. Cl. .................. 252/187.21; 252/186.1; 252/187.1; 252/187.23; 252/187.24; 252/187.25; 252/187.26; 252/187.27; 252/187.28; 252/187.29; 252/187.3; 424/661

(58) Field of Search ............ 252/187.21, 186.1, 252/187.1, 187.23, 187.24, 187.25, 187.26, 187.27, 187.28, 187.29, 187.3; 424/661

(56) References Cited

U.S. PATENT DOCUMENTS

| | | | |
|---|---|---|---|
| 4,104,190 A | 8/1978 | Hartshorn | 252/187 R |
| 4,547,381 A | 10/1985 | Mason et al. | 426/316 |
| 5,399,288 A | 3/1995 | Marzouk et al. | 252/186.21 |
| 6,197,215 B1 * | 3/2001 | Pitochelli | 252/186.1 |

* cited by examiner

*Primary Examiner*—Jill Warden
*Assistant Examiner*—Monique T. Cole
(74) *Attorney, Agent, or Firm*—Armstrong, Westerman & Hattori, LLP

(57) ABSTRACT

A dry disinfectant composition for the production of aqueous solutions of chlorine dioxide of predetermined concentration is formulated of a mixture of lithium hypochlorite, sodium bisulfate and sodium chlorite. Special liquid and dry formulations are also contemplated for convenience of use, for quality assurance and for safety.

17 Claims, 1 Drawing Sheet

COMPOSITION FOR GENERATING CHLORINE DIOXIDE

RELATED APPLICATIONS

This application is a continuation-in-part of my prior application Ser. No. 09/257,627 filed Feb. 25, 1999 and now U.S. Pat. 6,197,215.

FIELD OF THE INVENTION

The invention finds applicability in fields where chlorine dioxide is generally used and particularly in the fields of disinfection and odor treatment, as well as, demand studies.

BACKGROUND OF THE INVENTION

The inventor has been developing solid mix formulations which will allow for the preparation of small quantities (normally one liter, but the same mix has been used to prepare up to 300 gallons or more) of an aqueous chlorine dioxide solution at repeatable and reproducible concentrations of up to and beyond 3,000 mg/l. In addition, the inventor has developed a wet and dry formulation for purposes of enhanced use.

Prior Art Patents

The chemistry for producing chlorine dioxide from dry components is well known and has been the subject of at least two patents, U.S. Pat. No. 5,399,288 and U.S. Pat. No. 4,104,190.

Marzouk et al in U.S. Pat. No. 5,399,288 teaches solid chlorine dioxide releasing compositions involving the use of a triazinetrione.

Hartshorn in U.S. Pat. No. 4.104,190 discloses a dry composition for releasing chlorine dioxide containing dichloroisocyanurate as the chlorine releasing compound.

Mason et al in U.S. Pat. No. 4,547,381 discloses a dry composition for sustained, controlled production of gaseous chlorine dioxide. No water is added to the dry composition to produce the chlorine dioxide. Moreover, note that the composition of Mason et al requires a dry inert diluent added to the active chlorine dioxide producing components. On the other hand, applicant's formulation does not require an inert diluent added to the active ingredients. Moreover, the inventor intends to use his composition in a manner distinct from Mason et al. That is, the inventor intends to use his composition in water, Mason et al do not.

The prior art does not teach the chlorine dioxide releasing compositions yielding solutions of predetermined concentration as taught by the herein disclosed invention.

Chlorine dioxide is a powerful, selective oxidant which finds use as a drinking water disinfectant, in cooling tower biological control, as a paper pulp bleach, a disinfectant in fruit, vegetable and poultry processing, for oil well and water injection well stimulation, in wastewater treatment, as an algaecide, and as an odor control agent. Almost all applications use gaseous chlorine dioxide as a dilute aqueous solution, usually at or below 3,000 ppm. This solution cannot be supplied to the end user ready for use. Aside from the unattractive economics of shipping a solution which is 99.7% water, shipment is forbidden by the DOT. Unlike liquefied chlorine, the condensed liquefied gas cannot be prepared and shipped in cylinders because of its extreme shock sensitivity. As a consequence, it is necessary that chlorine dioxide be prepared on site at the time of use by combining the appropriate precursors in a chlorine dioxide generator. These precursors include aqueous solutions of sodium chlorate or sodium chlorite, mineral or organic acids, aqueous or gaseous chlorine, sodium hypochlorite, or some combination of these, usually as aqueous solutions which are metered out in the appropriate amounts and combined under controlled conditions by the chlorine dioxide generator. The need for a generator has usually limited use of this oxidant to those situations which justified the expense of installing and maintaining the necessary equipment. Typically, the smallest generators commercially available make 30 pounds per day of gaseous chlorine dioxide. This invention allows the use of chlorine dioxide treatment in those situations where the product's unique capabilities are attractive, but which are too small to justify installation and use of a generator.

OBJECTS OF THIS INVENTION

The inventor expects there to be strong consumer interest in using non-toxic, inorganic dry mix packets to prepare chlorine dioxide and particularly for disinfecting drinking water. The inventor's intent is that the composition be employed both for short term use, such as, for preparing emergency drinking water, and for treating drinking water for daily consumption.

An important object of this invention is to provide a disinfecting composition without there being organic material present.

The herein disclosed invention has for an object providing a convenient way to prepare small quantities of chlorine dioxide which are safe for treating drinking water or for disinfecting fruits and vegetables and like products.

Another object of this invention is to produce a product which will give consistent results for disinfecting drinking water and especially poor quality drinking water which might be available in emergency situations.

A further object of this invention is to produce a product which is non-toxic when used as directed.

A major object of this invention is to produce a dry mix formulation which produces hypochlorous acid precursor on addition of water to the dry mix and which does not introduce objectionable organic by-products.

A still further object of this invention is to produce a combination dry and wet mix product which can be safely transported and can be used to accurately make large volume solutions of chlorine dioxide.

A critical part of this invention is the incorporation in the mix of a component which rapidly generates hypochlorous acid on contact with water. The inventor has developed a formulation suitable for the disinfection of drinking water. The new formulation contains three components: lithium hypochlorite, sodium bisulfate and sodium chlorite. The inventor has found that when these three solids in various quantities are added to a suitable quantity of water, the solids dissolve completely within one minute, and at the end of this brief period, have generated as much chlorine dioxide as the mix will form. The system generates chlorine above its solubility in water, and so the gas bubbles generated agitate the mixture and speed up reaction and solution of components. The rapidity of solution is surprising.

These and other objects of the present invention will become apparent from a reading of the following specification taken in conjunction with the enclosed drawing.

The effective amounts of the components of this invention are exemplified in the description and the examples.

BRIEF SUMMARY OF THE INVENTION

The dry mix formulation which is the heart of this invention incorporates lithium hypochlorite, 25–30 weight % LiOCl; sodium hydrogen sulfate (synonym: sodium bisulfate), NaHSO$_4$; and 80% dry solid sodium chlorite, NaClO$_2$.

Regarding the LiOCl$_2$ 25–30 wt %, the composition used in this invention is:

| COMPONENT | WT % |
|---|---|
| Lithium Hypochlorite | 25–30 |
| Sodium Chloride | 36 |
| Sodium Sulfate | 13 |
| Potassium Sulfate | 6 |
| Lithium Chloride | 4 |
| Lithium Carbonate | 2 |
| Lithium Chlorate | 2 |
| Lithium Hydroxide | 1 |
| Water | 7 |

The ingredients other than the lithium hypochlorite were inert and are not necessary to the performance of this invention. These inert components could be substituted with other inert compatible salts or the like as would be understood by those skilled in the art. A product providing the above formulation can be obtained from FMC Corporation or could be readily formulated by those skilled in the art.

The 80% dry solid sodium chlorite product employed in the examples of this invention is as follows:

| COMPONENT | SPECIFICATIONS |
|---|---|
| Sodium Chlorite, wt % as NaClO$_2$ | 77.5–82.5 |
| Sodium Chlorate, wt % as NaClO$_3$ | 4 max. |
| Sodium Chloride, wt % as NaCl | 11–19 |
| Sodium Hydroxide, wt % as NaOH | 3 max. |
| Sodium Carbonate, wt % as Na$_2$CO$_3$ | 2 max. |
| Sodium Sulfate, wt % as Na$_2$SO$_4$ | 3 max. |
| Hydrogen Peroxide, wt % as H$_2$O$_2$ | 0.01 max. |
| Water (by difference), wt % | 6 max. |

It is to be understood that the main active ingredient is the Sodium Chlorite and the other components are ancillary thereto and are deemed to be inert. These inert ingredients are not essential to the invention and could be replaced by other like inert ingredients as readily understood by those skilled in the art.

In its preferred embodiment, the lithium hypochlorite and sodium bisulfate are packaged together in one pouch or container, and the sodium chlorite is packed separately in another pouch or container which may or may not be connected. This two-packet system has two purposes; one is to improve storage stability, especially under conditions of elevated temperature. The other purpose is to allow the components to be mixed in a prescribed manner to ensure a specific known, final concentration of generated chlorine dioxide. A single packet containing a stable mix of all three components is also possible, but this single packet must be maintained at a temperature below 140° F. (preferably below 125° F.) to avoid decomposition. This single mix has a further disadvantage of generating chlorine dioxide of variable and unpredictable concentrations as a function of variations in the method of mixing (See FIG. 1).

A solid mix has been devised which rapidly generates chlorine dioxide when added to water. The mix will allow the generation of a known quantity of aqueous chlorine dioxide in a predictable concentration to be used for the disinfection of drinking water, fruits and vegetables, biocidal treatment of cooling towers, treatment of medical waste and other disinfection, and most especially industrial applications, which are too small to justify the installation of a chlorine dioxide generator. The mix can also be used for small scale odor control.

Properly formulated, the three component mixture of this invention can be used to disinfect fruits and vegetables at a concentration of chlorine dioxide in water as low as 1–2 ppm. A concentration of about 100 ppm would be operative for use as a deodorant.

The separated two-pack products of this invention have been found to be thermally stable in tests performed at a temperature of above 140° F.

Figure 1:
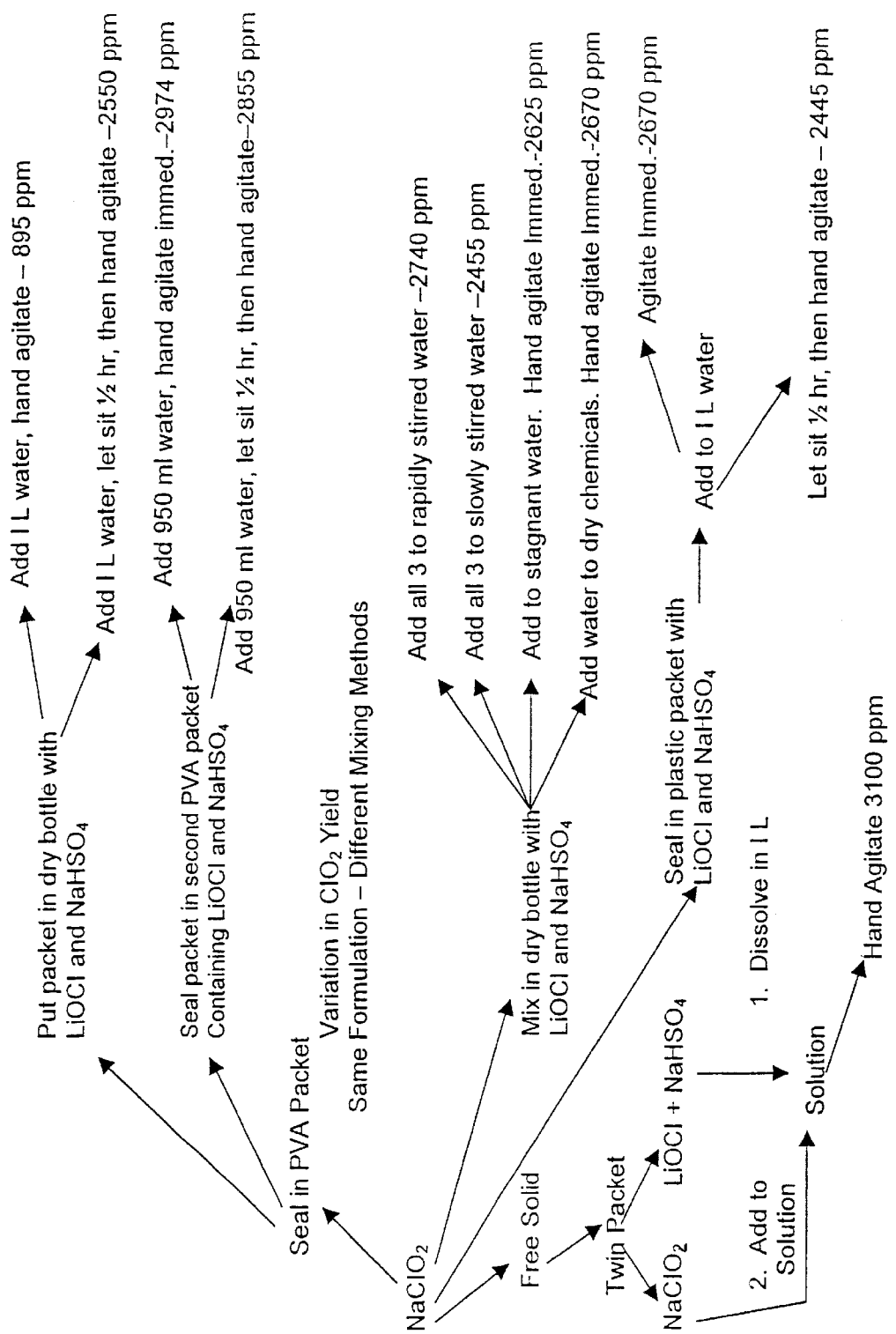
With reference to FIG. 1, a diagram shows variation of ClO$_2$ yield depending upon the method of mixing. In all of the tests shown in FIG. 1, the formulations were of the same amounts differing only in the method of mixing.

Part of the art of this invention involves the manner of mixing the components. As the attached chart (FIG. 1) shows, different types of mixes containing the exact same quantities of each of the components will give chlorine dioxide solutions of differing concentrations depending on how the components are mixed with water. It is an intent of this invention to formulate a product which allows a user in the field to prepare a solution of chlorine dioxide of known and desired concentration predictably and reliably, so that a dosage rate can be selected and the chlorine dioxide applied without the need for chlorine dioxide assay.

In one embodiment of the invention, the inventor intends to provide packages of the disinfectant formulations in water soluble packets for ease of use. In that way, instead of having to empty the contents of a packet in water, the entire soluble packet and/or packets and their contents can be placed in water to be treated.

As a matter of convenience, a mix has been devised which can reliably give one liter of 3000 ppm chlorine dioxide when the components are combined with water in a specified manner. This mix is provided in packs called an Activator Packet and a Chlorite Packet:

| Activator Packet contains: | LiOCl (25–30 weight %): | 6.12 g |
|---|---|---|
| | and | |
| | NaHSO$_4$ | 7.7 g |
| Chlorite Packet contains: | 80% NaClO$_2$: | 5.6 g |

With the LiOCl and the NaClO$_2$, the balance of the product is an inert ingredient.

When the Activator Packet and the Chlorite Packet are properly added to a liter of water, substantially 3000 ppm of chlorine dioxide will be produced. Component ratios based on chlorite are approximately:

| NaClO$_2$ = 1.0 | (80 weight percent) |
|---|---|
| LiOCl = 1.09 | (25–30 weight percent) |
| NaHSO$_4$ = 1.38 | |

It should be understood that the invention is not limited to compositions which generate only one liter of solution, but can be adjusted to produce any volume less than or more than one liter. While the actual weight of each component will be apportioned depending on the intended volume of final solution, the ratio of components must be maintained to ensure efficient chlorite conversion and the best yield and purity of chlorine dioxide.

It should also be understood that the selection of a chlorine dioxide concentration of 3,000 ppm is arbitrary, and that solutions substantially below and above this concentration are possible. Solutions in excess of 5,000 ppm have been prepared with properly formulated mixtures of components. Generation of very dilute solutions (1–100 ppm) is possible by using appropriately scaled quantities of each of the reactants, however, to ensure rapid, complete and accurate chlorite conversion, it is preferred that a more concentrated solution be prepared and subsequently diluted to the desired concentration.

It is to be understood that if an exact final concentration of chlorine dioxide is not required, lithium hypochlorite, sodium bisulfate and sodium chlorite in substantial amounts as taught by this invention can be used.

The user has the flexibility in combining the Activator Packet and the Chlorite Packet with the appropriate volume of water in any manner he chooses, however in order to ensure that the concentration of the final solution be as intended, the packets must be used in a prescribed manner, namely, complete dissolution of the Activator Packet, which requires less than one minute, and then the addition and rapid complete solution of the Chlorite Packet. When the chlorite is completely dissolved, the solution is at full strength and ready to be used. It is necessary to use this two-step method in sequence in order to ensure that prior to the addition of chlorite, the lithium hypochorite has been completely converted to hypochlorous acid by reaction with the acid produced on solution and hydrolysis of the sodium bisulfate. Hypochlorous acid reacts rapidly with chlorous acid formed by reaction of chlorite anion with protons supplied by the proton donor to give high yields of chlorine dioxide.

$$HOCl + 2HClO_2 \rightarrow 2ClO_2 + HCl + H_2O$$

If instead of the adding the components sequentially as required, the chlorite is simultaneously combined with activator, either by adding both packets of the two packet system, or by adding the single packet of the one packet system, a competitive reaction between hypochlorite anion and chlorite anion occurs which converts some of the chlorite to inert chlorate, reducing the quantity of chlorite available for conversion and, thereby, reducing the yield of chlorine dioxide. If directions as to how the components are mixed or agitated are not followed, a chlorine dioxide solution of unpredictable concentration is prepared, robbing the invention of an important part of its value, namely, that of producing a chlorine dioxide solution of predictable concentration, eliminating the need for field assay prior to use and allowing the end user to apply chorine dioxide at the correct dosage rate intended.

As referred to earlier, in addition to the two-packet system, all three components can also be combined into a stable mix in a single packet. This mix is somewhat more thermally sensitive than the two-packet system, but nevertheless is stable if kept below 140° F. On addition of this one pack formulation embodiment to water, it is impossible to avoid the competitive reaction between hypochlorite anion and chlorite anion which generates chlorate and depletes chlorite. When using the one pack formulation, it is necessary to adjust the quantities and ratios of the components to allow for some hypochlorite and chlorite loss. The component quantities and ratios for the one packet formulation are:

| LiOCl 25–30 weight %: | 6.16 g |
| NaHSO$_4$: | 7.7 g |
| NaClO$_2$ (80 weight %): | 6.33 g |

The ratios, based on chlorite are:
NaCaClO$_2$=1.0
LiOCl=0.97
NaHSO$_4$ 1.22

While this single packet system offers improved convenience over the two packet system, it is not the preferred embodiment. Unless specific directions are followed, the manner of mixing the solids into water will vary with the user. This variation will affect how the solid components are juxtaposed and agitated in the suspension before dissolving, thereby allowing a variable reaction between the hypochlorite anion and the chlorite anion, and thereby affecting the course of both the competitive and desired reactions. Because of the unpredictable degree to which chlorite will participate in the competitive reaction and the consequent effect on the final concentration of chlorine dioxide solution prepared, the one bag method, while it allows preparation of satisfactory and usable chorine dioxide solutions, is not preferred for applications which require close control over the chlorine dioxide dosage.

In the invention herein disclosed in many instances precise amounts and ratios have been set forth, however some variances of the amounts and ratios are expected to yield effective results as readily understood by those skilled in the art.

Lithium hypochlorite has advantages over calcium hypochlorite. For example, calcium hypochlorite dissolves too slowly to serve as a source of a significant quantity of hypochlorous acid, and has an objectionably strong chlorine odor (lithium hypochlorite has comparatively little chlorine odor) and when used with NaHSO$_4$ calcium hypochlorite forms solid calcium sulfate precipitate, resulting in low yields of chlorine dioxide with significant amounts of calcium sulfate solids impurity.

In its broadest sense, the herein disclosed invention embodies a product capable of being used for disinfection and/or oxidation comprising effective amounts of lithium hypochlorite, sodium bisulfate and sodium chlorite. Ideally, the lithium hypochlorite and sodium bisulfate are packaged together and the sodium chlorite is packaged alone. The product is supplied in the packages in substantially the following ratio:
NaClO$_2$=1.0
LiOCl=1.09
NaHSO$_4$=1.38

These ratios are of substantial amounts and can be varied as understood by those skilled in the art.

There is disclosed a method for preparing an active chlorine dioxide disinfecting solution comprising dissolving the contents of an Activator Pack containing LiOCl and NaHSO$_4$ in water and then shortly thereafter rapidly adding the Chlorite Pack containing NaClO$_2$ to said water containing therein the dissolved contents of the Activator Pack.

The active ingredients can be packaged in three individual packs.

The herein disclosed invention envisions methods for disinfecting a surface desired to be disinfected comprising applying to said surface the disclosed active ingredients added to water. In addition, fruits and vegetables can be disinfected, or waste water can be deodorized by the disclosed active ingredients added to water.

The inventor has continued to make improvements to his chlorine dioxide producing compositions. One of the improvements made by the inventor is the formulation of a "Dry and Wet Mix" composition. This formulation was created out of concern for Department of Transportation (DOT) regulations as well as NFPA and local fire code regulations limiting the storage of 80% dry sodium chlorite.

While the all dry-mix formulation is an effective disinfectant, it presents a shipping problem. That is, the DOT regulations forbid air shipment of dry chlorite along with a corrosive.

Dry chlorite is classified as a 5.1 oxidizer.

While the lithium hypochlorite contained in the activator packet is also classed as a 5.1 oxidizer, it can be packaged together with sodium bisulfate, which is classed as a corrosive, because the mixture has been determined to be corrosive solid, acidic, inorganic, N.O.S. 8, UN3260, packaging group 2 [contains metallic salts].

With the activator classed as a corrosive, and the dry chlorite classed as a 5.1 oxidizer, the DOT forbids shipment by air as a dual packet. If shipment by air is desired, the chlorite oxidizer and corrosive activator must be packaged separately; they can be shipped on the same plane, but in separate DOT approved packages.

The hazardous nature of sodium chlorite is due to its ability in the dry state to supply oxygen which in the event of fire could fuel the fire or be explosive.

Packaging dry chlorite presents several problems:

1. Certain types of manufactured chlorite are flaked, and as such difficult to pack and accurately measure for proper weight when dispensing small quantities.
2. Some geographic locations have a severe restriction on the physical quantity of dry chlorite allowed to be on site in compliance with local fire codes; thus, creating a problem for both the packager and the end user.
3. Dry chlorite is very hygroscopic and tends to pack, making it difficult to dispense during packaging.

These problems are immediately remedied if we substitute 25% aqueous sodium chlorite for the dry chlorite. For example:

1. Liquids can be dispensed accurately.
2. Hygroscopicity is no longer a problem.
3. Liquid chlorite is classified by the DOT as a corrosive, so the 5.1 oxidizer classification is no longer applied.
4. A corrosive can be shipped with a corrosive, meaning the shipping options are broader and less complicated, especially for air cargo.
5. Fire codes no longer limit the allowed chlorite on site.
6. From a preparation point of view, the system is less sensitive to sequence-of-mixing variations, improving the probability that the expected concentration will be accurately prepared.

These advantages are significant, and the "wet and dry" formulation may completely replace dry formulation for all but some specialized applications.

Another consideration of this invention deals with component ratios and how they are altered to accomplish the predictable preparation of large volumes of dilute chlorine dioxide solutions, as opposed to a small volume of concentrated chlorine dioxide.

In the past, if it was desired to prepare a multi-gallon volume of chlorine dioxide at some concentration significantly less than 3,000 ppm (which the formulation our application is designed to prepare), then it was necessary to first dilute a one liter volume of 3,000 ppm to the desired 150 ppm or 300 ppm, or whatever amount, using the proper amount of dilution water. In order to guarantee the concentration of the generated chlorine dioxide, it was necessary to make up the chlorine dioxide in a small volume, and then dilute the already-formed chlorine dioxide. If an attempt was made to take the same quantities of precursors and dissolve them directly in several gallons of water (instead of a liter) to prepare the dilute chlorine dioxide solution in one step, it was found that the final concentration of the dilute mix was unpredictable, and significantly below what might normally be expected if complete conversion of chlorite to chlorine dioxide took place.

The inventor has discovered that this unpredictability can be eliminated and a dilute chlorine dioxide solution of any desired concentration prepared, in a single step, in a large volume of water if sufficient proton donor is added to drop the pH of the full volume of water into the acid range. To accomplish this, the ratio of lithium hypochlorite to chlorite remains unchanged from that used for concentrated solutions, with the absolute quantities being chosen to prepare the concentration sized to the specific concentration desired. What must change is the quantity of sodium bisulfate added. If the sodium bisulfate quantity is sized to maintain the ratio normally used for the small-volume 3,000 ppm batches, then the quantity of bisulfate added is too small to overcome the buffering capacity of the dilution water in the large scale batch, and the pH will not move sufficiently into the acid range. What is needed is significantly more bisulfate to drop the pH of the solution into the acid range, because the lithium hypochlorite/chlorite conversion to chlorine dioxide will not take place properly unless the solution is acidic.

Accordingly, large batches of dilute chlorine dioxide of predictable concentration can be prepared by maintaining the lithium hypochlorite/chlorite ratio the same as used for the 3,000 ppm preparations, and sizing this ratio to produce the final desired concentration, while significantly increasing the quantity of sodium bisulfate used so that the pH of the final mix is in the 3–5 range.

EXAMPLES OF WET-DRY MIX

Example A

Provide in separate containers
Container 1
  4 gms Sodium bisulfate and 1.14 gms Lithium hypochlorite (25%)
Container 2
3.36 ml of 25% aqueous sodium chlorite
When the contents of container 1 and container 2 are added to a gallon of water, they will produce 150 ppm of chlorine dioxide at pH 3.5.

Example B

Provide in separate containers
Container 1
  40.0 gms sodium bisulfate and 11.4 gms lithium hypochlorite (25%) Container 2
  33.6 ml of 25% aqueous sodium chlorite
When the contents of container 1 and container 2 are added to a gallon of water, they will produce 300 ppm of chlorine dioxide at a pH of 3.8.

Example C

In making dilute solutions of 150 to 300 ppm of chorine dioxide per gallon of water, a "wet and dry" formulation comprising an activator mix of 4 grams of sodium bisulfate and 1.14 grams of lithium hypochlorite (25%) are first dissolved completely per gallon of water. When fully dissolved, 3.36 ml of 25% aqueous sodium chlorite solution is added per gallon of water. After completely mixing, the chlorine dioxide concentration was 150 ppm, and the pH of the solution was 3.5. Doubling the quantities of reactants used to make the 150 ppm solution results in the production of a 300 ppm solution of chlorine dioxide.

Example D

To make 5 gallons of solution containing 300 ppm of chlorine dioxide, a mix of 40.0 grams of sodium bisulfate and 11.4 grams of lithium hypochlorite (25%) are fully dissolved in 5 gallons of water. A 33.6 ml volume of 25% aqueous sodium chlorite is added to the dissolved activator, and a solution containing 300 ppm of chlorine dioxide having a pH of 3.8 is produced.

Examples A–D are exemplary only. The important consideration is that pH of the solution be brought within the prescribed acid range.

The herein disclosed invention envisions a kit for producing chlorine dioxide comprising in separate containers of aqueous sodium chlorite in a first container and dry lithium hypochlorite along with sodium bisulfate in the second container so that the kit and components are able to be safely transported without fear of hazard.

The invention encompasses a method of preparing chlorine dioxide comprising adding effective amounts of lithium hypochlorite and sodium bisulfate to water in sufficient amount to reduce pH into the acid range and then adding sodium chlorite to the acidified solution.

Many advantages accrue from applicant's invention:

1) Chlorine dioxide is generated with ease and in a predictable concentration.
2) No pre-mixing or measurement of ingredients is required.
3) Applications too small to justify a generator will find it convenient to employ the inventive product.
4) No toxic or unpleasant organic residue accompanies the use of the inventive composition.
5) The components are soluble in and react rapidly in very cold water (3° C).

It is to be understood that the amounts of ingredients herein set for are substantial amount as readily understood by those skilled in the art.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. A product capable of producing chlorine dioxide, consisting essentially of effective amounts of lithium hypochlorite, sodium bisulfate and sodium chlorite.
2. A product capable of producing chlorine dioxide comprising effective amounts of lithium hypochlorite, sodium bisulfate and sodium chlorite wherein the lithium hypochlorite and sodium bisulfate are packaged together and the sodium chlorite is packaged alone.
3. A product capable of producing chlorine dioxide comprising effective amounts of lithium hypochlorite, sodium bisulfate and sodium chlorite each packaged in an individual packet.
4. The product of claim 2 wherein the lithium hypochlorite is present in substantially 6.12 g, the sodium bisulfate is present in substantially 7.7 g and the sodium chlorite is present in substantially 5.6 g.
5. A product capable of producing chlorine dioxide comprising the following ingredients present in substantially the following ratio:

| | |
|---|---|
| Sodium chlorite | 1.00 |
| Lithium hypochlorite | 1.09 |
| Sodium bisulfate | 1.38 |

6. A method for preparing an active chlorine dioxide solution comprising (1) dissolving the contents of an Activator Pack containing lithium hypochlorite and sodium bisulfate in water and (2) thereafter adding a Chlorite Pack containing sodium chlorite to said water containing therein the dissolved contents of the Activator Pack and in substantially the ratio of 6.12 g. of lithium hypochlorite, 7.7 g. of sodium bisulfate and 5.6 g. of sodium chlorite.
7. A method of insuring the potability of water comprising adding the product of claim 1 to water.
8. A product of claim 1 which is contained within a one pack formulation consisting essentially of the following ratio: 1.0 part sodium chlorite to 0.97 part of lithium hypochlorite to 1.22 part of sodium bisulfate.
9. The product of claim 1 comprising a one pack formulation containing substantially 6.16 g of lithium hypochlorite; 7.7 g of sodium bisulfate and 6.33 of sodium chlorite to be added to a liter of water to produce substantially a 3,000 ppm chlorine dioxide solution.
10. A method for preparing a composition which comprises substantially 3,000 ppm of chlorine dioxide per liter comprising adding the product of claim 4 to a liter of water in an amount effective to disinfect said water.
11. A method for disinfecting a surface desired to be disinfected comprising applying to said surface the product of claim 1 added to water.
12. A method for disinfecting fruits and vegetables comprising applying to the surface of said fruits and vegetables the product of claim 1 mixed with water.
13. A method of deodorization of waste water comprising adding to said waste water to be deodorized the product of claim 1.
14. A product capable of producing chlorine dioxide the product comprising lithium hypochlorite, sodium bisulfate and sodium chlorite wherein the sodium chlorite is provided dissolved in water in a first container; and sodium bisulfate and lithium hypochlorite are provided in a dry form in a second container.
15. The product of claim 14 wherein the components are present in containers and, in substantially the amounts set forth, Container 1
    4 grams sodium bisulfate and 1.14 grams lithium hypochlorite (25%)
Container 2
    3.36 ml of 25% aqueous sodium chlorite so that when the components are properly added to a gallon of water, a composition of 150 ppm of chlorine dioxide at a pH of 3.5 will be produced.

16. A method of preparing chlorine dioxide comprising adding effective amounts of lithium hypochlorite and sodium bisulfate to water in sufficient amount to reduce pH into the acid range and then adding sodium chlorite to the acidified solution.
17. The method of claim 16 wherein the acid range is about pH of 3–5.

* * * * *